US009220416B2

United States Patent
Blank et al.

(10) Patent No.: US 9,220,416 B2
(45) Date of Patent: Dec. 29, 2015

(54) HEAT FLUX BALANCED THERMOMETER FOR MEASURING HUMAN CORE TEMPERATURE

(75) Inventors: Molly Annalise Buckley Blank, Bellevue, WA (US); Michael Jack Sinclair, Kirkland, WA (US); William Thomas Blank, Bellevue, WA (US)

(73) Assignee: Microsoft Technology Licensing, LLC, Redmond, WA (US)

( * ) Notice: Subject to any disclaimer, the term of this patent is extended or adjusted under 35 U.S.C. 154(b) by 743 days.

(21) Appl. No.: 13/530,710

(22) Filed: Jun. 22, 2012

(65) Prior Publication Data

US 2013/0341315 A1  Dec. 26, 2013

(51) Int. Cl.
*H05B 1/00* (2006.01)
*A61B 5/01* (2006.01)
*G01K 13/00* (2006.01)
*A61B 5/00* (2006.01)

(52) U.S. Cl.
CPC ............... *A61B 5/01* (2013.01); *G01K 13/002* (2013.01); *A61B 5/0022* (2013.01); *A61B 2560/0252* (2013.01); *A61B 2562/0271* (2013.01)

(58) Field of Classification Search
CPC ....... G01K 1/165; G01K 13/002; G01K 7/42; A61B 5/01; A61B 5/0022; A61B 2562/12; A61B 2562/0271; A61B 2560/0252
See application file for complete search history.

(56) References Cited

U.S. PATENT DOCUMENTS

| 7,597,668 | B2 | 10/2009 | Yarden |
| 2009/0306536 | A1 | 12/2009 | Ranganathan et al. |
| 2011/0051776 | A1 | 3/2011 | Bieberich et al. |
| 2011/0264001 | A1* | 10/2011 | Cheung et al. ............... 600/549 |
| 2013/0331728 | A1* | 12/2013 | Sun et al. ..................... 600/549 |

OTHER PUBLICATIONS

Buller, et al., "Estimation of Human Internal Temperature from Wearable Physiological Sensors", In Proceedings of AAAI Publications, Twenty-Second IAAI Conference, Jul. 13-17, 2008, 6 pages.
Kimberger, et al., "Accuracy and Precision of a Novel Non-Invasive Core Thermometer", In Proceedings of British Journal of Anaesthesia, vol. 103, Issue 2, Apr. 20, 2009, pp. 226-231.
Rossi, et al., "Predicting Body Core Temperature using Non-Invasive Sensors", Available at: http://www.empa.ch/plugin/template/empa/*/1112660, Published on Sep. 30, 2011, 21 pages.
Liu, et al., "Temperature Sensor Array System for Thermal Diagnostics on Human Disease", In Proceedings of 23rd Annual International Conference of the IEEE on Engineering in Medicine and Biology Society, Oct. 25-28, 2001, 5 pages.
(Continued)

*Primary Examiner* — Shawntina Fuqua
(74) *Attorney, Agent, or Firm* — Alin Corie; Sandy Swain; Micky Minhas

(57) ABSTRACT

Different advantageous embodiments provide an apparatus comprising one or more heating elements, a plurality of sensors, insulation, and a processor. The plurality of sensors includes at least a skin temperature sensor and an oven temperature sensor. The insulation is configured to thermally isolate the skin temperature sensor form the oven temperature sensor. The processor is configured to receive temperature data from the plurality of sensors and to control the one or more heating elements using the temperature data received.

20 Claims, 4 Drawing Sheets

Human Core Temperature Detection Environment
300

(56) References Cited

OTHER PUBLICATIONS

Liden, et al., "Characterization and Implications of the Sensors Incorporated into the SenseWear Armband for Energy Expenditure and Activity Detection", Available at: http://sensewear.bodymedia.com/site/docs/papers/Sensors.pdf, Oct. 12, 2011, 7 pages.
Huizenga, et al., "Skin and Core Temperature Response to Partial- and Whole-body Heating and Cooling", Available at: http://escholarship.org/uc/item/30c8q5j4, Aug. 24, 2004, 11 pages.
Kirk, et al., "Infra-red Thermometry: The Reliability of Tympanic and Temporal Artery Readings for Predicting Brain Temperature After Severe Traumatic Brain Injury", Critical Care 2009, Issue 13, vol. 3, R81, Published May 27, 2009, 9 pages.
Varela, et al., "Temperature Curve Complexity Predicts Survival in Critically Ill Patients", American Journal of Respiratory and Critical Care Medicine, vol. 174, May 11, 2006, pp. 290-298.
Werner, et al., "Preliminary Data on a New Non-Invasive Method to Measure Core Temperature with the Double Sensor under Cold Conditions", In Proceeding of RTO Human Factors and Medicine Panel (HFM) Symposium, Apr. 20-22, 2009, 16 pages.
Teunissen, et al., "Non-invasive Continuous Core Temperature Measurement by Zero Heat Flux", Physiological Measurement, vol. 32, No. 5, Mar. 28, 2011, 13 pages.
Kiyatkin, E.A., "Brain temperature fluctuations during physiological and pathological conditions," Eur J Appl Physiol, vol. 101, pp. 3-17, 2007.
Robinson, J., "Oesophageal, rectal, tympanic, and polmonary artery temperatures during cardiac surgery," Can J Anaesth, vol. 45, No. 4, pp. 317-323, 1998.
Mariak, Z., "Tympanic temperature reflects intracranial temperature changes in humans," Eur J Physiol, vol. 446, pp. 279-284, 2003.
Gunga, H.C., "A non-invasive device to continuously determine heat strain in humans," J Thermal Biology, vol. 33, pp. 297-307, 2008.
Gunga, H.C., "The Double Sensor; a non-invasive device to continuously monitor core temperature in humans on earth and in space," Respiratory Physiology and Neurobiology, vol. 169, pp. 563-568, 2009.
Varela, M., "Complexity analysis of the temperature curve: new informaiton from body temperature," Eur J Appl Physiol, vol. 89, pp. 230-237, 2003.
Fowler, L., "Establishing the presence of a body temperature rhythm in chimpanzees (*Pan troglodytes*) using a tympanic membrane thermometer," Primates, vol. 40, No. 3, pp. 499-508, 1999.
Matsukawa, T., "A comparison of four infrared tympanic thermometers with tympanic membrane temperatures measured by thermocouples," Can J Anaesth, vol. 43, No. 12, pp. 1224-1228, 1996.
Sehgal, A., "Comparison of tympanic and rectal temperature in febrile patients," Incian J of Pediatrics, vol. 69, pp. 305-308, 2002.
Masamune, T., "The usefulness of an earphone-type infrared tympanic thermometer during cardiac surgery with cardiopulmonary bypass: clinical report," J Anaesth, pp. 1-4, 2011.
Yamakage, M., "Evaluation of a newly developed monitor of deep body temperature," J Anesth, vol. 16, pp. 354-357, 2002.
Zeiner, A., "Non-invasive continuous cerebral temperature monitoring in patients with mild therapeutic hypothermia: an observational pilot study," Resuscitation, vol. 81, pp. 861-866, 2010.

* cited by examiner

HEAT FLUX BALANCED THERMOMETER FOR MEASURING HUMAN CORE TEMPERATURE

BACKGROUND

Measurements of human body temperature are useful for monitoring and determining a number of different factors. In a health environment, for example, measurement of human core body temperature may be beneficial in monitoring or identifying a health issue. Measurements of human core temperature generally involve considerably invasive methods, such as inserting thermal probes deep into body orifices. Due to the invasive nature of obtaining human core temperature readings, continuous monitoring is inhibited to limited activities.

Thermal sensors respond to changes in temperature with a measurement output. Thermal sensors are used in health environments to measure human body temperature. However, thermal sensors are sensitive to environmental changes in temperature. Therefore, it is desirable to have technology that addresses one or more of the issues discussed above in order to provide a non-invasive solution in a small form factor for continuously monitoring human core temperature over time.

SUMMARY

This Summary is provided to introduce a selection of representative concepts in a simplified form that are further described below in the Detailed Description. This Summary is not intended to identify key features or essential features of the claimed subject matter, nor is it intended to be used in any way that would limit the scope of the claimed subject matter.

Briefly, various aspects of the subject matter described herein are directed towards an apparatus comprising a plurality of sensors, one or more heating elements, insulation, and a processor. The plurality of sensors includes at least a skin temperature sensor and an oven temperature sensor. The insulation isolates the skin temperature sensor from the oven temperature sensor. The processor is configured to receive temperature data from the plurality of sensors and to control the one or more heating elements using the temperature data received.

Another aspect is directed towards a method for monitoring core temperature change. Skin temperature is detected. A determination is made as to whether the skin temperature detected is at equilibrium with an oven temperature. In response to a determination that the skin temperature detected is not at equilibrium with the oven temperature, a heating control value is changed.

Yet another aspect is directed towards a monitoring system comprising a sensor system and a processor. The sensor system is configured to detect core temperature data. The processor is configured to actively receive temperature data from the sensor system and to generate control signals for the one or more heating elements to achieve zero heat flux between a skin temperature sensor and the one or more heating elements.

Other advantages may become apparent from the following detailed description when taken in conjunction with the drawings.

BRIEF DESCRIPTION OF THE DRAWINGS

The present invention is illustrated by way of example and not limited in the accompanying figures, in which like reference numerals indicate similar elements. The advantageous embodiments, as well as a preferred mode of use, further objectives and advantages thereof, will best be understood by reference to the following detailed description of an advantageous embodiment of the present disclosure when read in conjunction with the accompanying drawings, wherein.

DETAILED DESCRIPTION

Various aspects of the technology described herein are generally directed towards an apparatus and method for non-invasive, continuous monitoring of human core temperature. As will be understood, a thermometer uses a control processor and a number of sensors separated by thermal isolating material and one or more heating elements configured to provide equilibrium between the core temperature and the thermometer in order to monitor and detect changes in core temperature over time.

While the various aspects described herein are exemplified with a health environment directed towards monitoring human core body temperature, it will be readily appreciated that other environments and subjects may benefit from the technology described herein. For example, the various aspects described herein may be used to monitor core temperature changes in a veterinary environment.

Thus, as will be understood, the technology described herein is not limited to any type of environment or subject for core temperature change detection and monitoring. As such, the present invention is not limited to any particular embodiments, aspects, concepts, protocols, structures, functionalities or examples described herein. Rather, any of the embodiments, aspects, concepts, protocols, structures, functionalities or examples described herein are non-limiting, and the present invention may be used in various ways that provide benefits and advantages in core temperature monitoring and change detection in general.

Figure 1:
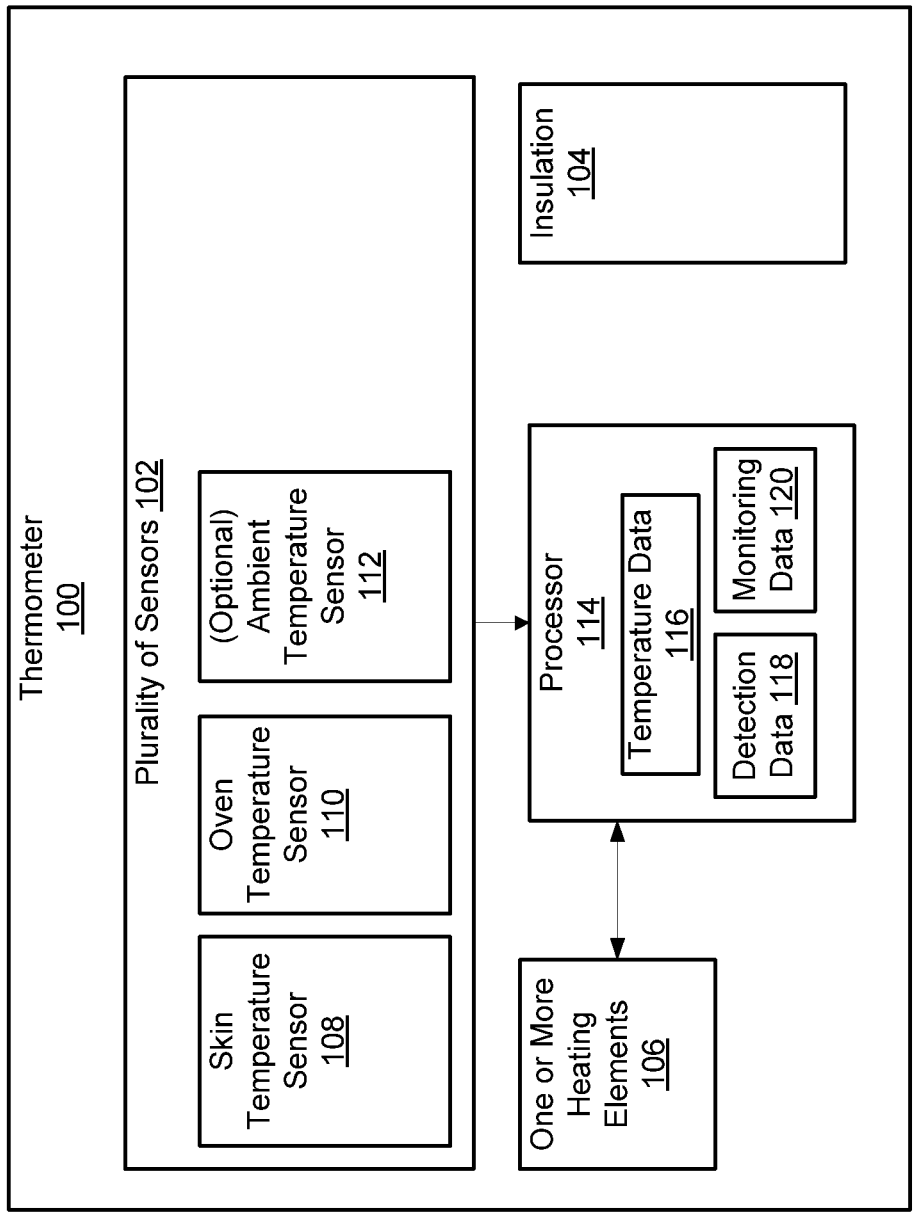
FIG. 1 is a block diagram illustrating an example of a thermometer in accordance with an advantageous example embodiment.

With reference now to the figures, FIG. 1 is an illustration of a thermometer in accordance with an advantageous embodiment of the present invention. A thermometer 100 may include a plurality of sensors 102, insulation 104, and one or more heating elements 106. The plurality of sensors 102 may be, for example, without limitation, thermocouple-based sensors, thermistor-based sensors, infrared-based sensors, and/or may be based upon any other suitable sensor technology for detecting and measuring temperature. The plurality of sensors 102 includes a skin temperature sensor 108 and an oven temperature sensor 110. As used herein, oven may refer to any type of electrical to thermal transducer that uses joule heating to raise the temperature of an object, for example. Optionally, the plurality of sensors 102 may also include an ambient temperature sensor 112.

The skin temperature sensor 108 is configured to detect the core temperature of a person using the thermometer 100. The oven temperature sensor 110 is configured to detect the temperature of the one or more heating elements 106. The optional ambient temperature sensor 112 is configured to detect the temperature of the ambient environment outside of and/or around the thermometer 100.

The insulation 104 may be, for example, without limitation, silicon, urethane foam, aero gel, rubber, vacuum vessel, and/or any other suitable material for insulating each of the plurality of sensors 102 from one another. The insulation 104 aids in reducing one or more of thermal radiance, conduction, or convection within the thermometer 100. For example, thermal radiance, or flux, may be reduced between the plurality of sensors 102 using the insulation 104. The one or more heating elements 106 may include, for example, without limitation, a ring heater, a chip resistor heater, a heat spreader, and/or any other suitable heating device. The one or more heating elements 106 are configured to heat the thermometer 100 until equilibrium is reached with the temperature detected by the skin temperature sensor 108 and the temperature detected by the oven temperature sensor 110. In this way, the thermometer 100 acts as if it were encapsulated, or embedded, within the skin of the person whose core body temperature is being monitored, for example. As a result, by equalizing the skin temperature and the heater temperature, the heat flux into and out of the skin temperature sensor 108 is zero, and therefore, the skin temperature becomes equal to the core body temperature, assuming no other thermal influences are present in the person being monitored.

The ambient temperature sensor 112 may be used to ensure that the skin temperature sensor 108 and the oven temperature sensor 110 are not affected by the ambient environment. For example, changes detected in the ambient environment using the ambient temperature sensor 112 may be mitigated by the processor 114.

The processor 114 may be any type of processing unit, including, without limitation, a microprocessor, microcontroller, central processing unit, and/or any other suitable processing device. The processor 114 may be implemented adjacent to the plurality of sensors 102, in one advantageous embodiment. In other advantageous embodiments, the processor 114 may be in communication with the plurality of sensors 102 and implemented remote from the plurality of sensors 102.

The processor 114 receives temperature data 116 from the plurality of sensors 102. The processor 114 uses the temperature data 116 received from the plurality of sensors 102 to control the one or more heating elements 106. In one illustrative example, when the processor 114 receives a temperature reading from the skin temperature sensor 108 that is higher than the temperature reading from the oven temperature sensor 110, the processor 114 may send signals to the one or more heating elements 106 to activate the one or more heating elements 106. In another illustrative example, when the processor 114 receives a temperature reading from the skin temperature sensor 108 that is at equilibrium with the temperature reading from the oven temperature sensor 110, the processor 114 may send instructions to the one or more heating elements 106 to deactivate the one or more heating elements 106. In this example, the one or more heating elements 106 and the processor 114 balance any heat flux and consume minimal power.

In one illustrative embodiment, the processor 114 stores the temperature data 116 received from the plurality of sensors 102. In another illustrative embodiment, the processor 114 generates detection data 118 using the temperature data 116 and any corresponding instructions sent to the one or more heating elements, for example. The detection data 118 may be temperature information generated by the plurality of sensors 102 and corresponding instructions to the one or more heating elements, if any, generated by the processor 114 over a period of time. In one advantageous embodiment, the detection data 118 may include a plurality of time stamps, for example. The processor 114 may store, transmit, and/or release the temperature data 116 and/or the detection data 118.

In another advantageous embodiment, the processor 114 may process the detection data 118 and generate monitoring data 120 for transmission to a user interface, for example. The monitoring data 120 may be, for example, without limitation, statistical information of core temperature change over time, analysis of core temperature change over time, diagnostic information based on core temperature change over time, and/or any other suitable information using the detection data 116.

Small changes in core body temperature can be an early indication of the onset of an infection, disease, or other illness. Each person may have a slightly different core body temperature at which homeostasis is achieved. Additionally, a person's regular daily activities can result in fluctuations in core body temperature in accordance with changes in environmental conditions and activity. A variety of biological mechanisms precisely control core body temperature. The detection of a change in core body temperature, rather than the actual value of that temperature, can be important in the early detection of disease, for example. When the skin is at equilibrium with the core body temperature, there is no flux or change in heat. Accordingly, when uniform heat is maintained between the skin sensor and the oven sensor, both of which are insulated from the environment, a change or flux in heat is driven by a change in core body temperature.

The plurality of sensors 102 may be relatively inexpensive sensors that are each calibrated against a National Institute of Standards (NIST) reference. One embodiment of the system uses a proportional, integral, and derivative (PID) controller, or a control loop feedback mechanism, to drive the heat flux to zero between the skin temperature sensor 108 and the oven temperature sensor 110. The PID controller calculates an error value as the difference between a measured temperature and a desired temperature, and adjusts the temperature data inputs received by the processor accordingly.

In one illustrative example, each of the plurality of sensors 102 may be calibrated by placing each sensor in a common environment, such as a heated oil bath, maintained at a specific temperature, for example. Each of the inexpensive sensors may have a different reading of the temperature of the common environment. The differential, or difference in readings, for each sensor is the error value. The error value is programmed into the firmware of the processor associated with each particular sensor, such that the differential is taken into account by the processing device when processing the temperature readings of each sensor. In other words, for two sensors in a thermometer, such as thermometer 100, the differential between the two sensors determined during calibration is programmed into processor 114, such that processor 114 adjusts the temperature information received from each of the two sensors before making a determination based on the temperature data.

Alternatively, pre-calibrated, yet more costly, thermistors may be used in thermometer 100 such that processor 114 may be programmed with predetermined firmware, or the like, corresponding to the calibration of the pre-calibrated thermistors.

FIG. 1 is intended as an example, and not as an architectural limitation for different embodiments. For example, in other advantageous embodiments, the plurality of sensors 102 may include communication means for receiving data from and transmitting data to the processor 114.

As used herein, the phrase "at least one of", when used with a list of items, means that different combinations of one or more of the items may be used and only one of each item in the list may be needed. For example, "at least one of item A, item B, and item C" may include, for example, without limitation, item A or item A and item B. This example also may include item A, item B, and item C or item B and item C.

As used herein, when a first component is connected to a second component, the first component may be connected to the second component without any additional components. The first component also may be connected to the second component by one or more other components. For example, one electronic device may be connected to another electronic device without any additional electronic devices between the first electronic device and the second electronic device. In some cases, another electronic device may be present between the two electronic devices connected to each other.

The different advantageous embodiments recognize and take into account that typical sensors used in health environments to measure human core body temperature are invasive and restrict the ambulatory function of the person being monitored. Additionally, typical sensors are often subject to mechanical interference and sensitive to environmental changes in temperature.

Thus, various aspects of the subject matter described herein are directed towards an apparatus comprising a plurality of sensors, one or more heating elements, insulation, and a processor. The plurality of sensors includes at least a skin temperature sensor and an oven temperature sensor. The insulation isolates the skin temperature sensor from the oven temperature sensor. The processor is configured to receive temperature data from the plurality of sensors and to control the one or more heating elements using the temperature data received.

Another aspect is directed towards a method for monitoring core temperature change. Skin temperature is detected. A determination is made as to whether the skin temperature detected is at equilibrium with an oven temperature. In response to a determination that the skin temperature detected is not at equilibrium with the oven temperature, a heating control value is changed.

Yet another aspect is directed towards a monitoring system comprising a sensor system and a processor. The sensor system is configured to detect core temperature data. The processor is configured to actively receive temperature data from the sensor system and to generate control signals for the one or more heating elements to achieve zero heat flux between a skin temperature sensor and the one or more heating elements.

Figure 2:
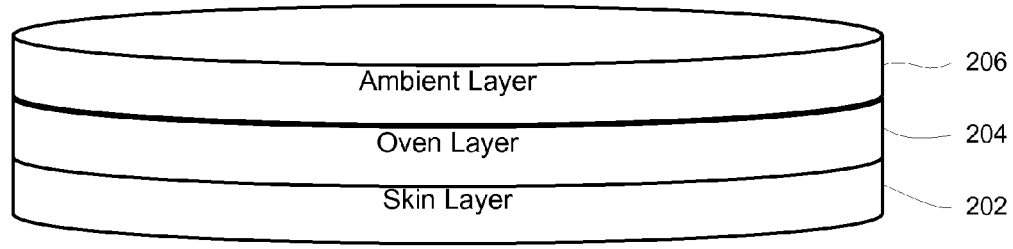
FIG. 2 is a block diagram illustrating an example of a sensor system layout in accordance with an advantageous example embodiment.

With reference now to FIG. 2, an illustration of a sensor system layout is depicted in accordance with an advantageous embodiment. The sensor system layout 200 includes a skin layer 202, an oven layer 204, and an ambient layer 206.

In this illustrative embodiment, the skin layer 202 may include a sensor, such as skin temperature sensor 108 in FIG. 1, insulated from the oven layer 204 by insulation, such as insulation 104 in FIG. 1, for example. The oven layer 204 may include one or more heating elements, such as the one or more heating elements 106 in FIG. 1, and a sensor, such as oven temperature sensor 110 in FIG. 1. The ambient layer 206 may include insulation, such as insulation 104 in FIG. 1, to isolate the oven layer from the ambient environment. Optionally, the ambient layer 206 may also include a sensor, such as ambient temperature sensor 112 in FIG. 1.

Communication means between the sensors, the heating elements, and a processor may be implemented in any one or more of the depicted layers, in one advantageous embodiment. In another advantageous embodiment, a microprocessor or other suitable processing device may be implemented in any one or more of the depicted layers.

The illustration of the sensor system layout 200 in FIG. 2 is not meant to imply physical or architectural limitations to the manner in which different advantageous embodiments may be implemented. Other components in addition and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments.

Figure 3:
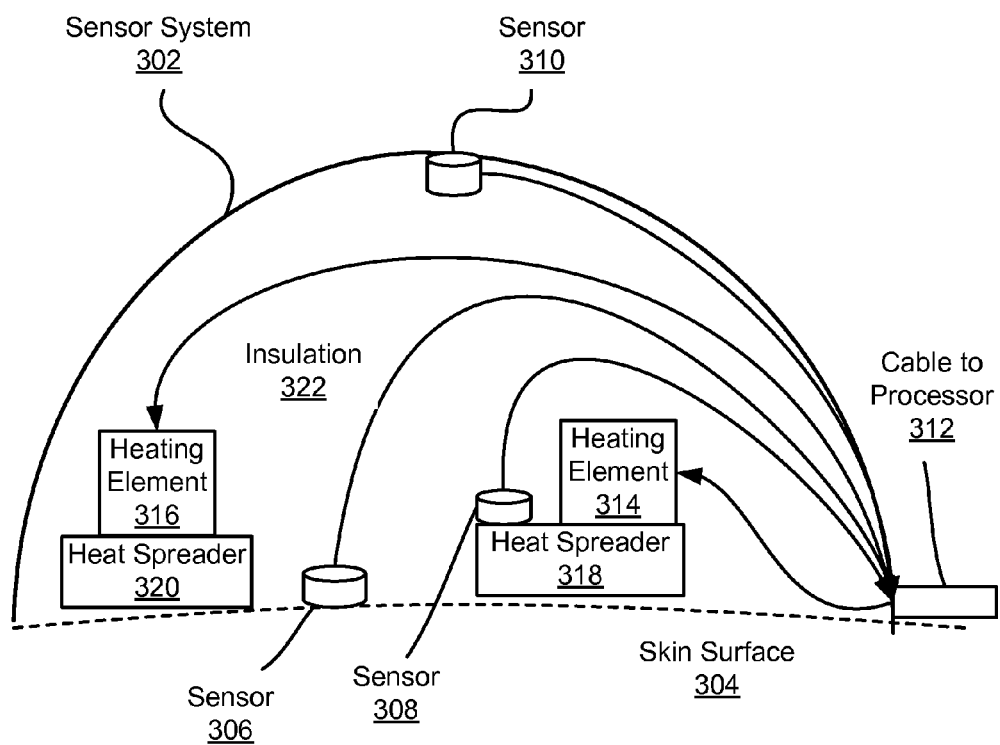
FIG. 3 is a block diagram illustrating an example of a human core temperature detection environment in accordance with an advantageous example embodiment.

With reference to FIG. 3, an illustration of a human core temperature detection environment 300 is depicted in accordance with an advantageous embodiment. The human core temperature detection environment 300 is an illustrative example of one environment in which an advantageous embodiment of thermometer 100 in FIG. 1 may be implemented.

The human core temperature detection environment 300 detects core temperature change in a person using a thermometer, such as the thermometer 100 in FIG. 1. In this illustrative embodiment, the human core temperature detection environment 300 depicts sensor system 302 affixed to and/or implemented upon the skin surface 304. In different illustrative embodiments, the sensor system 302 may be affixed to the skin surface of any area, such as, without limitation, a forehead, a sternum, an armpit, an area of the neck corresponding to the carotid artery, and/or any other suitable position on the external surface of a human body excluding extremities.

The sensor system 302 includes sensor 306, sensor 308, and sensor 310. Sensor 306 may be an illustrative example of one implementation of skin temperature sensor 108 in FIG. 1. Sensor 308 may be an illustrative example of one implementation of oven temperature sensor 110 in FIG. 1. Sensor 310 may be an illustrative example of one implementation of ambient temperature sensor 112 in FIG. 1.

Each of sensor 306, sensor 308, and sensor 310 are in communication with processor 312 using a communication means, such as a wireless signal or a cable, for example. Processor 312 may be an example of one implementation of processor 114 in FIG. 1. Temperature information detected by each of sensor 306, sensor 308, and sensor 310 is sent to the processor via the cable to processor 312. Instructions and/or signals may be transmitted from the processor to a heating element 314 and a heating element 316.

The heating element 314 may be coupled to a heat spreader 318, and the heating element 316 may be coupled to a heat spreader 320, in this illustrative example. The heating element 314, the heating element 316, the heat spreader 318, and the heat spreader 320 may be illustrative examples of one implementation of the one or more heating elements 106 in FIG. 1. In an illustrative example, the processer transmits instructions to activate the heating element 314 and the heating element 316. The heat spreader 318 and the heat spreader 320 may be, for example, any type of material with high thermal conductivity that allows the heat flux sourced from the heating elements to be conducted throughout the material of the heat spreader so that all parts of the heat spreader are at the same temperature. The heat spreader 318 and the heat spreader 320 spread the heat generated by the heating element 314 and the heating element 316 until the temperature detected by the sensor 308 is at equilibrium with the temperature detected by sensor 306.

Insulation 322 provides thermal isolation between the sensor 308 and the sensor 306, and further thermally isolates sensor 310 from sensor 308. The insulation 322 is an illustrative example of one implementation of the insulation 104 in FIG. 1.

The illustration of the human core temperature detection environment 300 in FIG. 3 is not meant to imply physical or architectural limitations to the manner in which different advantageous embodiments may be implemented. Other components in addition and/or in place of the ones illustrated may be used. Some components may be unnecessary in some advantageous embodiments. Also, the blocks are presented to illustrate some functional components. One or more of these blocks may be combined and/or divided into different blocks when implemented in different advantageous embodiments. For example, in one illustrative embodiment, the processor may be implemented within sensor system 302, and configured to transmit data to an external user interface.

Figure 4:
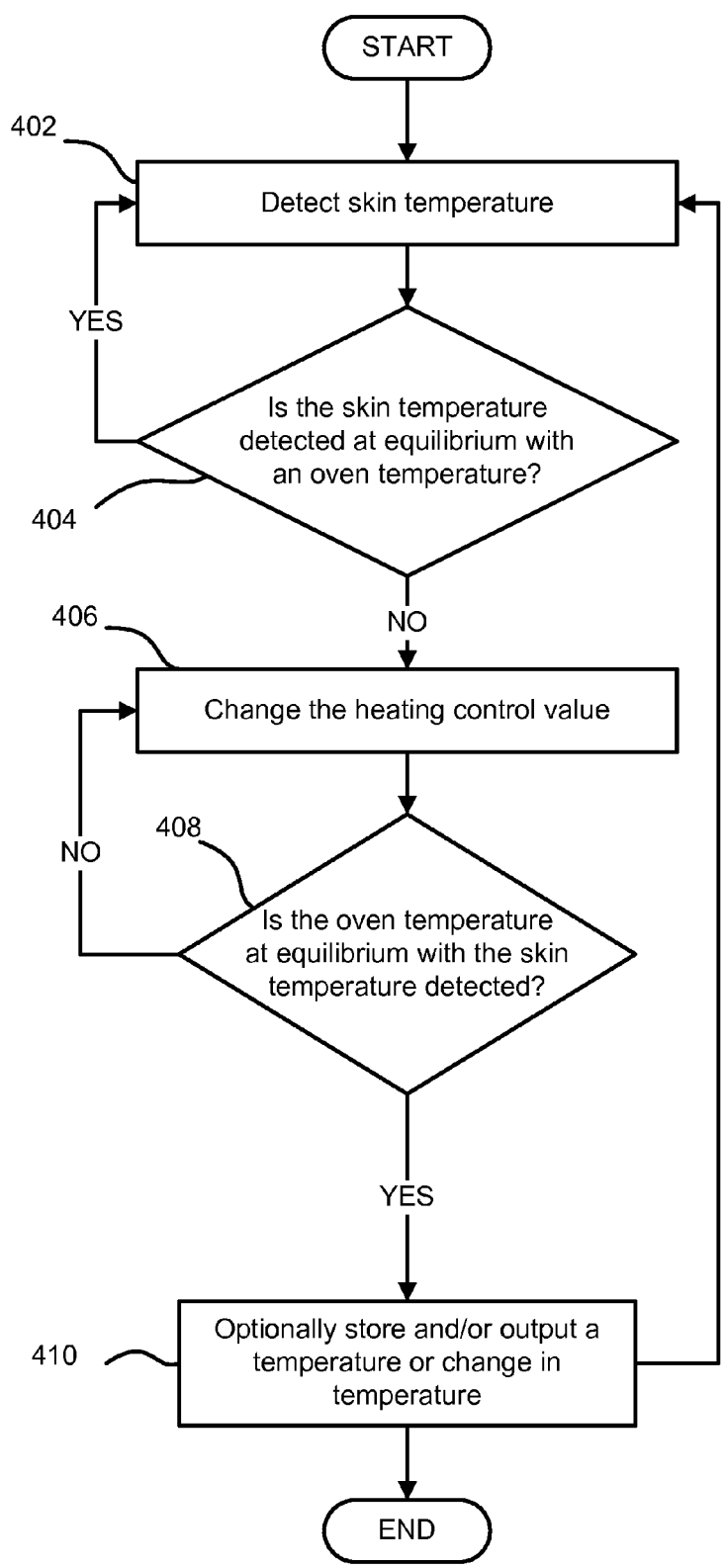
FIG. 4 is a flow diagram representative of example steps in monitoring core temperature change over time in accordance with an advantageous example embodiment.

With reference now to FIG. 4, an illustration of a flow diagram of monitoring core temperature change over time is depicted in accordance with an advantageous embodiment. The flow diagram in FIG. 4 represents an example process that may be implemented by a thermometer, such as the thermometer 100 in FIG. 1, for example.

The process begins by detecting skin temperature (operation 402). The skin temperature may be detected using a sensor, such as skin temperature sensor 108 in FIG. 1, for example. The process determines whether the skin temperature detected is at equilibrium with an oven temperature (operation 404). The determination may be made by a processor, such as processor 114 in FIG. 1, for example. The oven temperature data may be captured using an oven temperature sensor, for example, such as the oven temperature sensor 110 in FIG. 1.

In response to a determination that the skin temperature detected is at equilibrium with the oven temperature, the process returns to step 402. In response to a determination that the skin temperature detected is not at equilibrium with the oven temperature, the process changes the heating control value (operation 406). The heating control value may be, for example, the one or more signals sent by processor 114 to control the one or more heating elements 106 in FIG. 1. The processor will send heating control values to the one or more heating elements to increase or decrease the temperature of the one or more heating elements.

In an illustrative example, if the skin temperature detected is higher than the oven temperature detected, the heating control value may control the one or more heating elements to increase the oven temperature. In another illustrative example, if the skin temperature detected is lower than the oven temperature detected, the heating control value may control the one or more heating elements to decrease the oven temperature, even to the point of turning off the one or more heating elements. The process then determines whether the oven temperature is at equilibrium with the skin temperature detected (operation 408).

In response to a determination that the oven temperature is not at equilibrium with the skin temperature detected, the process returns to step 408. In response to a determination that the oven temperature is at equilibrium with the skin temperature detected, the process then optionally stores and/or outputs a temperature or change in temperature (operation 410), with the process terminating thereafter. Alternatively, the process may continuously monitor for change in core temperature by returning to step 402 following step 408. In this way, power consumption is kept at a minimum, with the heating elements controlled only as needed to maintain equilibrium with the body temperature detected.

The flowcharts and block diagrams in the different depicted embodiments illustrate example architecture, functionality, and operation of some possible implementations of apparatus, methods and computer program products. In this regard, each block in the flow diagram or block diagrams may represent a module, segment, or portion of computer usable or readable program code, which comprises one or more executable instructions for implementing the specified function or functions. In some alternative implementations, the function or functions noted in the block may occur out of the order noted in the figures. For example, in some cases, two blocks shown in succession may be executed substantially concurrently, or the blocks may sometimes be executed in the reverse order, depending upon the functionality involved.

The different advantageous embodiments can take the form of an entirely hardware embodiment, an entirely software embodiment, or an embodiment containing both hardware and software elements. Some embodiments are implemented in software, which includes but is not limited to forms, such as, for example, firmware, resident software, and microcode.

Furthermore, the different embodiments can take the form of a computer program product accessible from a computer usable or computer readable medium providing program code for use by or in connection with a computer or any device or system that executes instructions. For the purposes of this disclosure, a computer usable or computer readable medium can generally be any tangible apparatus that can contain, store, communicate, propagate, or transport the program for use by or in connection with the instruction execution system, apparatus, or device.

The computer usable or computer readable medium can be, for example, without limitation an electronic, magnetic, optical, electromagnetic, infrared, or semiconductor system, or a propagation medium. Non limiting examples of a computer readable medium include a semiconductor or solid state memory, magnetic tape, a removable computer diskette, a random access memory (RAM), a read-only memory (ROM), a rigid magnetic disk, and an optical disk. Optical disks may include compact disk-read only memory (CD-ROM), compact disk-read/write (CD-R/W) and DVD.

Further, a computer usable or computer readable medium may contain or store a computer readable or usable program code such that when the computer readable or usable program code is executed on a computer, the execution of this computer readable or usable program code causes the computer to transmit another computer readable or usable program code over a communications link. This communications link may use a medium that is, for example without limitation, physical or wireless.

A data processing system suitable for storing and/or executing computer readable or computer usable program code will include one or more processors coupled directly or indirectly to memory elements through a communications fabric, such as a system bus. The memory elements may include local memory employed during actual execution of the program code, bulk storage, and cache memories which provide temporary storage of at least some computer readable or computer usable program code to reduce the number of times code may be retrieved from bulk storage during execution of the code.

Input/output or I/O devices can be coupled to the system either directly or through intervening I/O controllers. These devices may include, for example, without limitation to keyboards, touch screen displays, and pointing devices. Different communications adapters may also be coupled to the system to enable the data processing system to become coupled to other data processing systems or remote printers or storage devices through intervening private or public networks. Non-limiting examples are modems and network adapters are just a few of the currently available types of communications adapters.

The different advantageous embodiments recognize and take into account that typical sensors used in health environments to measure human core body temperature are invasive and restrict the ambulatory function of the person being monitored. Additionally, typical sensors are often subject to mechanical interference and sensitive to environmental changes in temperature.

Thus, the different advantageous embodiments provide an apparatus and method for a power efficient, non-invasive core temperature monitoring and detection system in a small form factor for continuously monitoring core temperature changes over time. Due to the small size and non-invasive design, the different advantageous embodiments provide a monitoring system that can be utilized to monitor human core temperature continuously, throughout regular daily activity.

The description of the different advantageous embodiments has been presented for purposes of illustration and description, and is not intended to be exhaustive or limited to the embodiments in the form disclosed. Many modifications and variations will be apparent to those of ordinary skill in the art. Further, different advantageous embodiments may provide different advantages as compared to other advantageous embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

Example Operating Environment

Figure 5:
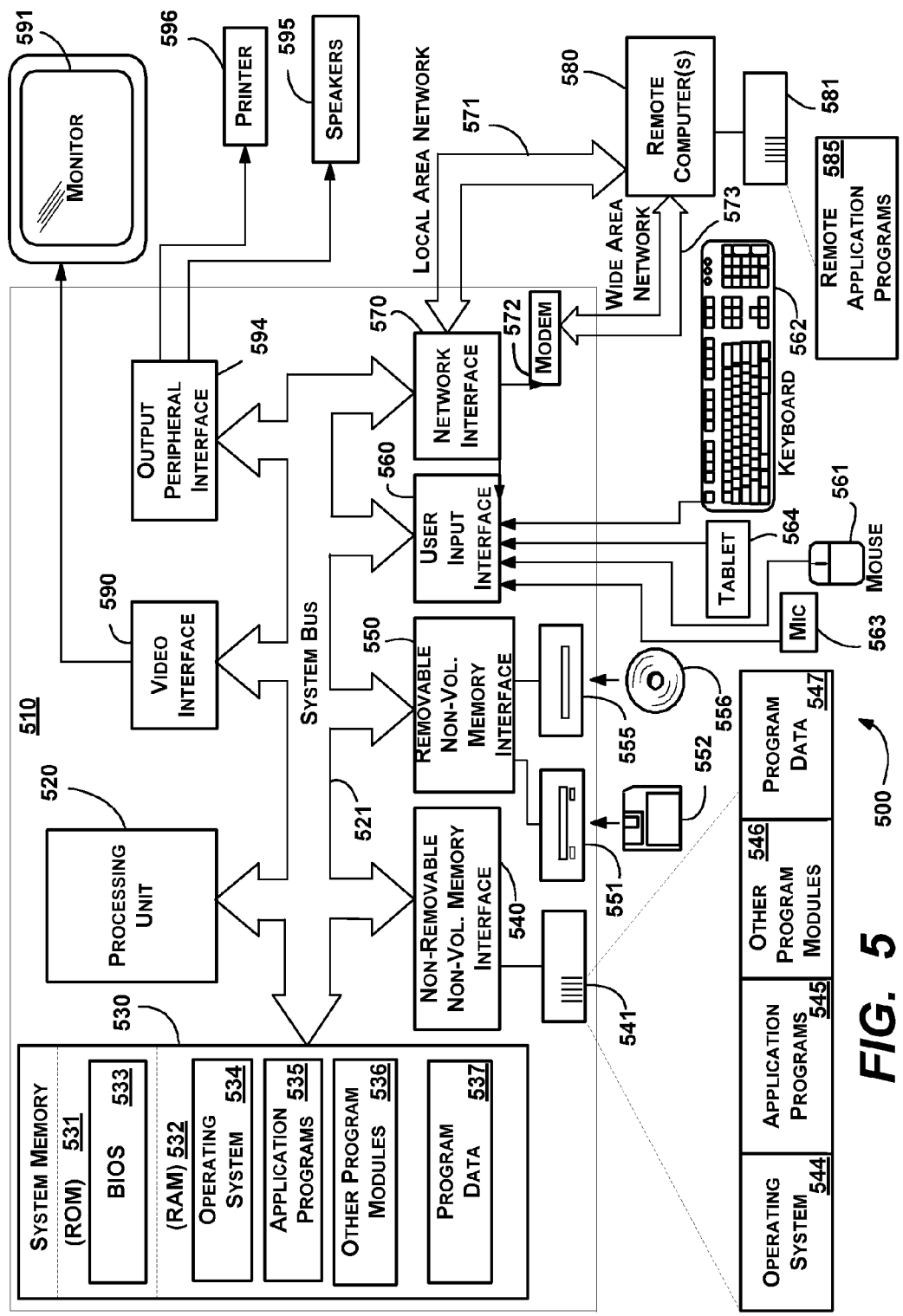
FIG. 5 is a block diagram representing an example computing environment into which aspects of the subject matter described herein may be incorporated.

With reference now to FIG. 5, an illustrative example of a suitable computing and networking environment 500 is provided, into which the examples and implementations of any of FIGS. 1-4 as well as any alternatives may be implemented. The computing system environment 500 is only one example of a suitable computing environment and is not intended to suggest any limitation as to the scope of use or functionality of the invention. Neither should the computing environment 500 be interpreted as having any dependency or requirement relating to any one or combination of components illustrated in the example operating environment 500.

The invention is operational with numerous other general purpose or special purpose computing system environments or configurations. Examples of well known computing systems, environments, and/or configurations that may be suitable for use with the invention include, but are not limited to: microcontrollers, personal computers, server computers, hand-held or laptop devices, tablet devices, multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, and so forth, which perform particular tasks or implement particular abstract data types. The invention may also be practiced in distributed computing environments where tasks are performed by remote processing devices that are linked through a communications network. In a distributed computing environment, program modules may be located in local and/or remote computer storage media including memory storage devices.

With reference to FIG. 5, an example system for implementing various aspects of the invention may include a general purpose computing device in the form of a computer 510. Components of the computer 510 may include, but are not limited to, a processing unit 520, a system memory 530, and a system bus 521 that couples various system components including the system memory to the processing unit 520. The system bus 521 may be any of several types of bus structures including a memory bus or memory controller, a peripheral bus, and a local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus also known as Mezzanine bus.

The computer 510 typically includes a variety of computer-readable media. Computer-readable media can be any available media that can be accessed by the computer 510 and includes both volatile and nonvolatile media, and removable and non-removable media. By way of example, and not limitation, computer-readable media may comprise computer storage media and communication media. Computer storage media includes volatile and nonvolatile, removable and non-removable media implemented in any method or technology for storage of information such as computer-readable instructions, data structures, program modules or other data. Computer storage media includes, but is not limited to, RAM, ROM, EEPROM, flash memory or other memory technology, CD-ROM, digital versatile disks (DVD) or other optical disk storage, magnetic cassettes, magnetic tape, magnetic disk storage or other magnetic storage devices, or any other medium which can be used to store the desired information and which can accessed by the computer 510. Communication media typically embodies computer-readable instructions, data structures, program modules or other data in a modulated data signal such as a carrier wave or other transport mechanism and includes any information delivery media. The term "modulated data signal" means a signal that has one or more of its characteristics set or changed in such a manner as to encode information in the signal. By way of example, and not limitation, communication media includes wired media such as a wired network or direct-wired connection, and wireless media such as acoustic, RF, infrared and other wireless media. Combinations of the any of the above may also be included within the scope of computer-readable media.

The system memory 530 includes computer storage media in the form of volatile and/or nonvolatile memory such as read only memory (ROM) 531 and random access memory (RAM) 532. A basic input/output system 533 (BIOS), containing the basic routines that help to transfer information between elements within computer 510, such as during start-up, is typically stored in ROM 531. RAM 532 typically contains data and/or program modules that are immediately accessible to and/or presently being operated on by processing unit 520. By way of example, and not limitation, FIG. 5 illustrates operating system 534, application programs 535, other program modules 536 and program data 537.

The computer 510 may also include other removable/non-removable, volatile/nonvolatile computer storage media. By way of example only, FIG. 5 illustrates a hard disk drive 541 that reads from or writes to non-removable, nonvolatile magnetic media, a magnetic disk drive 551 that reads from or writes to a removable, nonvolatile magnetic disk 552, and an optical disk drive 555 that reads from or writes to a removable, nonvolatile optical disk 556 such as a CD ROM or other optical media. Other removable/non-removable, volatile/nonvolatile computer storage media that can be used in the example operating environment include, but are not limited to, magnetic tape cassettes, flash memory cards, digital versatile disks, digital video tape, solid state RAM, solid state ROM, and the like. The hard disk drive 541 is typically connected to the system bus 521 through a non-removable memory interface such as interface 540, and magnetic disk drive 551 and optical disk drive 555 are typically connected to the system bus 521 by a removable memory interface, such as interface 550.

The drives and their associated computer storage media, described above and illustrated in FIG. 5, provide storage of computer-readable instructions, data structures, program modules and other data for the computer 510. In FIG. 5, for example, hard disk drive 541 is illustrated as storing operating system 544, application programs 545, other program modules 546 and program data 547. Note that these components can either be the same as or different from operating system 534, application programs 535, other program modules 536, and program data 537. Operating system 544, application programs 545, other program modules 546, and program data 547 are given different numbers herein to illustrate that, at a minimum, they are different copies. A user may enter commands and information into the computer 510 through input devices such as a tablet, or electronic digitizer, 564, a microphone 563, a keyboard 562 and pointing device 561, commonly referred to as mouse, trackball or touch pad. Other input devices not shown in FIG. 5 may include a joystick, game pad, satellite dish, scanner, or the like. These and other input devices are often connected to the processing unit 520 through a user input interface 560 that is coupled to the system bus, but may be connected by other interface and bus structures, such as a parallel port, game port or a universal serial bus (USB). A monitor 591 or other type of display device is also connected to the system bus 521 via an interface, such as a video interface 590. The monitor 591 may also be integrated with a touch-screen panel or the like. Note that the monitor and/or touch screen panel can be physically coupled to a housing in which the computing device 510 is incorporated, such as in a tablet-type personal computer. In addition, computers such as the computing device 510 may also include other peripheral output devices such as speakers 595 and printer 596, which may be connected through an output peripheral interface 594 or the like.

The computer 510 may operate in a networked environment using logical connections to one or more remote computers, such as a remote computer 580. The remote computer 580 may be a personal computer, a server, a router, a network PC, a peer device or other common network node, and typically includes many or all of the elements described above relative to the computer 510, although only a memory storage device 581 has been illustrated in FIG. 5. The logical connections depicted in FIG. 5 include one or more local area networks (LAN) 571 and one or more wide area networks (WAN) 573, but may also include other networks. Such networking environments are commonplace in offices, enterprise-wide computer networks, intranets and the Internet.

When used in a LAN networking environment, the computer 510 is connected to the LAN 571 through a network interface or adapter 570. When used in a WAN networking environment, the computer 510 typically includes a modem 572 or other means for establishing communications over the WAN 573, such as the Internet. The modem 572, which may be internal or external, may be connected to the system bus 521 via the user input interface 560 or other appropriate mechanism. A wireless networking component 574 such as comprising an interface and antenna may be coupled through a suitable device such as an access point or peer computer to a WAN or LAN. In a networked environment, program modules depicted relative to the computer 510, or portions thereof, may be stored in the remote memory storage device. By way of example, and not limitation, FIG. 5 illustrates remote application programs 585 as residing on memory device 581. It may be appreciated that the network connections shown are examples and other means of establishing a communications link between the computers may be used.

An auxiliary subsystem 599 (e.g., for auxiliary display of content) may be connected via the user interface 560 to allow data such as program content, system status and event notifications to be provided to the user, even if the main portions of the computer system are in a low power state. The auxiliary subsystem 599 may be connected to the modem 572 and/or network interface 570 to allow communication between these systems while the main processing unit 520 is in a low power state.

CONCLUSION

While the invention is susceptible to various modifications and alternative constructions, certain illustrated embodiments thereof are shown in the drawings and have been described above in detail. It should be understood, however, that there is no intention to limit the invention to the specific forms disclosed, but on the contrary, the intention is to cover all modifications, alternative constructions, and equivalents falling within the spirit and scope of the invention.

What is claimed is:

1. An apparatus comprising:
one or more heating elements;
a plurality of sensors comprising at least a skin temperature sensor and an oven temperature sensor, wherein the oven temperature sensor is configured to measure a temperature of the one or more heating elements;
insulation configured to thermally isolate the skin temperature sensor from the oven temperature sensor; and
a processor configured to:
receive temperature data from the plurality of sensors;
control the one or more heating elements using the temperature data received;
generate detection data using the received temperature data and information corresponding to instructions associated with the control of the one or more heating elements, the detection data including a plurality of temperature measurements associated with a plurality of timestamps; and
generate monitoring data based on an analysis of the detection data.

2. The apparatus of claim 1, wherein the skin temperature sensor is configured to measure a temperature of an external human surface.

3. The apparatus of claim 1, further comprising:
one or more heat spreaders corresponding to the one or more heating elements.

4. The apparatus of claim 1, wherein the processor is further configured to process the temperature data from the plurality of sensors to derive both absolute temperature and change in temperature.

5. The apparatus of claim 1, wherein the processor is further configured to increase a heating control value or decrease a heating control value to control the one or more heating elements using the temperature data received from the plurality of sensors.

6. The apparatus of claim 1, further comprising:
an ambient temperature sensor, wherein the ambient temperature sensor is configured to measure a temperature of an ambient environment.

7. The apparatus of claim 1, wherein the insulation includes at least one of a urethane foam, an aero gel, silicone, vacuum vessel, or rubber.

8. The apparatus of claim 1, wherein the plurality of sensors includes at least one of a thermocouple-based sensor, a thermistor-based sensor, or an infrared sensor.

9. The apparatus of claim 1, wherein the monitoring data includes at least one of statistical information of core temperature change over time for a monitored subject, analysis of the core temperature change over time for the monitored subject, or diagnostic information based on the core temperature change over time for the monitored subject.

10. A method comprising:
detecting, by a monitoring system, skin temperature of a monitored subject;
determining whether the detected skin temperature is at equilibrium with an oven temperature of the monitoring system;
responsive to a determination that the detected skin temperature is not at equilibrium with the oven temperature, changing a heating control value; and
storing detection data, including a timestamp and at least one of a temperature measurement or a change in temperature.

11. The method of claim 10 wherein changing the heating control value further comprises:
increasing the temperature of the oven.

12. The method of claim 10 wherein changing the heating control value further comprises:
decreasing the temperature of the oven.

13. The method of claim 10 further comprising:
generating monitoring data based on an analysis of the detection data, the monitoring data including at least one of statistical information of core temperature change over time for the monitored subject, analysis of the core temperature change over time for the monitored subject, or diagnostic information based on the core temperature change over time for the monitored subject; and
transmitting the generated monitoring data to a user interface.

14. A monitoring system comprising:
a sensor system configured to detect core temperature data, the sensor system comprising one or more heating elements, a skin temperature sensor, and an oven temperature sensor; and
at least one processor communicatively coupled to the sensor system and configured to:
actively receive temperature data from the sensor system over time;
generate control signals for the one or more heating elements to achieve zero heat flux between a skin temperature sensor and the one or more heating elements based on the received temperature data;
process the received temperature data to generate detection data, including a plurality of temperature measurements associated with a plurality of timestamps;
analyze the detection data to generate monitoring data; and
responsive to a detection of a change in the core temperature data, generate an event notification for output via a user interface.

15. The monitoring system of claim 14, wherein the skin temperature sensor is configured to measure skin surface temperature, and wherein the oven temperature sensor is configured to measure a temperature of the one or more heating elements.

16. The monitoring system of claim 14, wherein the processor is configured to receive the core temperature data from the thermometer and process the core temperature data to detect changes in core temperature over time.

17. The monitoring system of claim 14, further comprising:
a communication system configured to provide communication between the sensor system and the at least one processor.

18. The monitoring system of claim 14, wherein the change in core temperature data indicates onset of at least one of an infection, disease, or illness.

19. The monitoring system of claim 14, wherein the processor includes a control loop feedback mechanism configured to:
calculate an error value as a difference between a measured temperature and a desired temperature; and
adjust the received temperature data based on the error value.

20. The monitoring system of claim 14, wherein the core temperature data is measured from the external skin surface of a human.

* * * * *